US010881499B2

(12) United States Patent
Timmerman

(10) Patent No.: US 10,881,499 B2
(45) Date of Patent: Jan. 5, 2021

(54) BONE TENDON CONSTRUCTS AND METHODS OF TISSUE FIXATION

(71) Applicant: Arthrex, Inc., Naples, FL (US)

(72) Inventor: Laura A. Timmerman, Walnut Creek, CA (US)

(73) Assignee: ARTHREX, INC., Naples, FL (US)

(*) Notice: Subject to any disclaimer, the term of this patent is extended or adjusted under 35 U.S.C. 154(b) by 415 days.

(21) Appl. No.: 14/464,230

(22) Filed: Aug. 20, 2014

(65) Prior Publication Data

US 2015/0057750 A1 Feb. 26, 2015

Related U.S. Application Data

(60) Provisional application No. 61/868,326, filed on Aug. 21, 2013.

(51) Int. Cl.
*A61F 2/08* (2006.01)
*A61B 17/04* (2006.01)
*A61B 17/06* (2006.01)

(52) U.S. Cl.
CPC ........ *A61F 2/0811* (2013.01); *A61B 17/0401* (2013.01); *A61B 17/06166* (2013.01); *A61B 2017/0404* (2013.01); *A61B 2017/06185* (2013.01); *A61F 2002/087* (2013.01); *A61F 2002/0852* (2013.01); *A61F 2002/0882* (2013.01)

(58) Field of Classification Search
CPC .............. A61F 2/0811; A61F 2002/087; A61F 2002/0882; A61F 2002/0852; A61B 17/06166; A61B 17/0401; A61B 2017/06185; A61B 2017/0404
See application file for complete search history.

(56) References Cited

U.S. PATENT DOCUMENTS

| 5,562,669 | A | * | 10/1996 | McGuire ............ A61B 17/1637 606/86 R |
| 6,533,802 | B2 | | 3/2003 | Bojarski et al. |
| 6,716,234 | B2 | | 4/2004 | Grafton et al. |
| 8,439,976 | B2 | | 5/2013 | Albertorio et al. |
| 8,460,379 | B2 | | 6/2013 | Albertorio et al. |

(Continued)

OTHER PUBLICATIONS

Athrex. All-Inside ACL RetroConstruction with Bone-Tendon-Bone Grafts. Brochure, 2011.*

(Continued)

*Primary Examiner* — Jerrah Edwards
*Assistant Examiner* — Rokhaya Diop
(74) *Attorney, Agent, or Firm* — Carlson, Gaskey & Olds

(57) ABSTRACT

Techniques and reconstruction systems for ligament repair and fixation. A bone tendon graft is prepared by folding the bone block over a suspensory fixation device (for example, a knotless suture construct such as a knotless, adjustable, self-cinching suture loop/button construct, a suture, cross-pin, or screw, etc.). A flexible strand is then used to suture the bone plug to the tendon so that the overall graft is shortened significantly and the suspensory fixation device is securely attached. The technique does not require passage of the suspensory fixation device through the bone block which makes the graft passage easier since the graft is pulled from the tip. The technique also allows shortening of the overall graft.

23 Claims, 6 Drawing Sheets

(56) References Cited

U.S. PATENT DOCUMENTS

| | | | |
|---|---|---|---|
| 2004/0267273 A1* | 12/2004 | Whittaker | A61B 17/1714 606/96 |
| 2008/0046009 A1 | 2/2008 | Albertorio et al. | |
| 2008/0228271 A1* | 9/2008 | Stone | A61F 2/08 623/13.12 |
| 2010/0249929 A1* | 9/2010 | Kurz | A61F 2/08 623/13.14 |
| 2010/0256677 A1* | 10/2010 | Albertorio | A61B 17/0401 606/232 |
| 2010/0324676 A1* | 12/2010 | Albertorio | A61B 17/0401 623/13.14 |
| 2013/0096612 A1* | 4/2013 | Zajac | A61B 17/0469 606/232 |

OTHER PUBLICATIONS

Athrex_All Inside ACL RetroConstruction with BoneTendonBone Grafts_2011 (Brochure).*
F. Alan Barber, "Flipped Patellar Tendon Autograft Anterior Cruciate Ligament Reconstruction." Arthroscopy: The Journal of Arthroscopic and Related Surgery, vol. 16, No. 5, pp. 483-490, Jul.-Aug. 2000.
ACL Graft Choices, Centers for Orthopaedics, Experience in Motion, http://www.orthoassociates.com/SP11B35/, pp. 1-9, Jul. 11, 2013.
ACL TightRope RT, Advancing ACL TightRope Fixation in a New Direction, Arthrex, http://acltightrope.arthrex.com, 2010.
Arthrex Allograft Graftlink, Surgical Technique, www.arthrex.com., 2013.

* cited by examiner

BONE TENDON CONSTRUCTS AND METHODS OF TISSUE FIXATION

CROSS-REFERENCE TO RELATED APPLICATIONS

This application claims the benefit of U.S. Provisional Application No. 61/868,326, filed Aug. 21, 2013, the disclosure of which is incorporated by reference in its entirety herein.

FIELD OF THE INVENTION

The present invention relates to the field of surgery reconstruction and, more particularly, to joint or ligament reconstruction techniques and associated fixation and reconstruction devices.

BACKGROUND OF THE INVENTION

Reconstructive surgeries, particularly anterior cruciate ligament (ACL) reconstruction, are well-known in the art. In general, these methods involve drilling a tunnel through the tibia, drilling a closed tunnel (socket) into the femur, inserting a substitute ACL graft into the tunnels, and securing the grafts to the walls of the tibial and femoral tunnels using interference screws or the like. Other methods of ACL reconstruction include using a button/loop construct for fixation, such as disclosed in U.S. Pat. No. 6,533,802 and U.S. Publication No. 2008/0046009.

There are a number of choices available to the orthopedic surgeon in determining which graft is best for a patient undergoing reconstructive surgery. For example, in ACL knee surgery, the patellar tendon bone-tendon-bone (BTB) graft continues to be the "gold standard" graft choice. One of the advantages of this construct is that, because the bone-tendon interface is quite strong, the surgeon only has to fix the block of bone in the bone tunnel rather than trying to fix the soft tissue itself. One disadvantage, however, is that the BTB graft is typically too long to fit into ACL tunnels with the bone block positioned correctly. Flipping the bone block or folding it (by rotating the bone plug about 180° proximally onto the tendon) allows shortening of the graft but makes the graft passage and fixation difficult.

Methods of adjusting the length of a bone tendon graft are needed, as well as methods of attaching a bone tendon graft (which is optionally shortened) to a suspensory fixation device for easy passage. Also needed are methods of preparing a bone tendon graft for ACL reconstruction that allow shortening of the overall graft length and fixation with a suspensory fixation device.

SUMMARY OF THE INVENTION

The present invention provides techniques and reconstruction systems for ligament repair and fixation. A bone tendon graft is prepared by folding the bone block over a suspensory fixation device (for example, a fixed loop, a tensionable loop, a knotless suture construct such as a knotless, adjustable, self-cinching suture loop/button construct, a suture, crosspin, or screw, etc.). A flexible strand is then used to suture the bone plug to the tendon so that the overall graft is shortened significantly and the suspensory fixation device is securely attached.

The novel technique of the present invention does not require passage of the suspensory fixation device through the bone block which makes the graft passage easier since the graft is pulled from the tip. The technique also allows shortening of the overall graft.

These and other features and advantages of the invention will be more apparent from the following detailed description that is provided in connection with the accompanying drawing and illustrated exemplary embodiments of the invention.

DETAILED DESCRIPTION OF THE PREFERRED EMBODIMENTS

Figure 1:
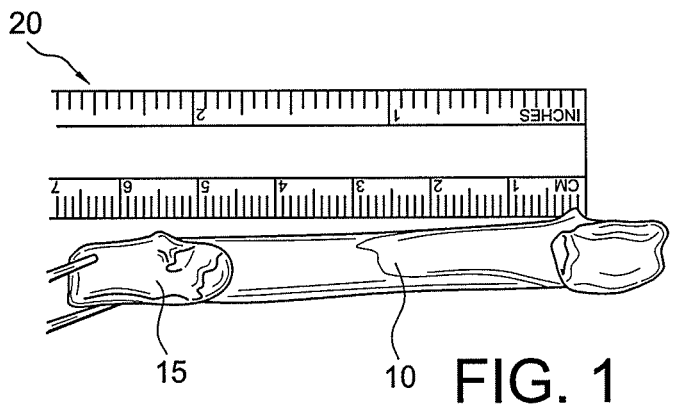
FIGS. 1-9 illustrate steps of a method of assembling a reconstruction system (an exemplary bone tendon graft attached to a suspensory fixation device) according to an exemplary embodiment of the present invention.

The present invention provides reconstruction systems for ligament repair and insertion techniques that employ a bone tendon graft with a suspensory fixation device.

According to an exemplary embodiment, the reconstruction system of the present invention comprises a suspensory fixation device in an exemplary form of a knotless suture construct, for example, a closed loop of flexible material such as an ACL TightRope®, a loop/button construct such as a standard loop/button construct, a suture, crosspin, or screw, etc. attached to a bone tendon graft. Small drill holes are placed through the bone plug/block and the bone block is folded over the suspensory fixation device. A flexible material such as suture or fiberloop is then employed to suture the bone plug to the tendon by passing a needle through the holes in the bone. The overall graft is shortened and the suspensory fixation device is securely attached to it. The technique does not require passage of the suspensory fixation device through the bone block which makes the graft passage easier since the graft is pulled from the tip. The technique also allows shortening of the overall graft. The technique allows shortening of the graft as well as attachment of a suspensory device for easy passage. If desired, and depending on the characteristics of the surgical repair, the technique may be repeated for the other end of the graft, i.e., for a bone-tendon-bone (BTB) graft.

The present invention also provides a method of ligament repair with a bone tendon graft by inter alia the steps of: (i) providing a tunnel or socket from a first bone surface and to a second bone surface; (ii) providing a reconstruction system (surgical integrated system) including a suspensory fixation device attached to a bone tendon graft; (iii) folding/flipping the bone block of the bone tendon graft over the suspensory fixation device to shorten the length of the bone tendon graft; (iv) securing the bone tendon graft to the suspensory fixation device by securing the bone block to the tendon portion of the bone tendon graft; and (v) securing the bone tendon graft within the bone tunnel.

Another exemplary method of tissue fixation according to the present invention comprises the steps of: (i) providing a bone tunnel; (ii) providing a knotless suture construct including a button and a loop of flexible material (which may be fixed or may have an adjustable length); (iii) assembling the knotless suture construct with a bone tendon graft including a bone block integral with a tendon, by folding the bone block over the tendon (and rotating the bone block about 180° proximally onto the tendon to allow shortening of the tendon) and then securing the bone block to the tendon and to the knotless suture construct, to form a button/graft construct; (iv) advancing the button/graft construct through the bone tunnel; and (v) securing the button/graft construct within the bone tunnel (optionally, by adjusting the length of the adjustable loop).

As detailed below, the surgical constructs comprise a tensionable construct with an adjustable, self-locking knotless flexible closed loop connected to a bone tendon construct (a bone tendon graft or a bone tendon bone (BTB) construct). The bone block is rotated about 180° proximally onto the tendon portion of the bone tendon graft or BTB graft (to shorten the overall length of the bone tendon graft), and then securely attached to the tendon (to also securely attach the flexible closed loop) by suturing, for example, or other known methods in the art. The tensionable construct may be a simple fixed loop (a continuous loop with a fixed length, and which may be rigid or flexible) or may be a tensionable, adjustable loop. The tensionable construct may optionally include a fixation device (for example, a button) securely attached to the adjustable loop. If desired, a splicing device (suture passing instrument or shuttle/pull device) may be included with the tensionable construct to aid in the formation of the final splice of the adjustable, self-locking knotless flexible closed loop. The tensionable construct may be adjustable in length and allows the surgeon the ability to customize the device to each patient and seat the graft against the wall of the bone tunnel or socket. The adjustments are self-locking and the fixation device minimizes the compressive forces on the bone block.

According to an exemplary embodiment, the tensionable construct is provided as a pre-assembled or pre-packaged construct. The pre-assembled tensionable construct may be assembled with BTB grafts or other tissue grafts such as a bone tendon graft, at the time of surgery, to form integrated systems for tissue repairs and reconstructions. During the assembly, the self-locking flexible adjustable closed loop is provided around tissue graft (for example, around a bone tendon block or a BTB block, and not through it).

The integrated systems of the present invention allow formation of the final fixation device with a knotless self-locking mechanism that allows the user (for example, the surgeon) to control the tension of the strand on the tissue to be attached to bone.

Referring now to the drawings, where like elements are designated by like reference numerals, FIGS. 1-9 illustrate steps for the assembling of reconstruction system 100 (surgical integrated system 100) of the present invention comprising a bone tendon graft 20 attached to a suspensory fixation device 50 which may include, for example, a fixed loop (a flexible loop with a fixed length) or a tensionable construct such as a closed, knotless, adjustable loop of flexible material having an adjustable perimeter. According to an exemplary-only embodiment, and as detailed below, reconstruction system 100 comprises a suspensory fixation device 50 with a closed flexible loop and a bone block 15 with a ligament graft 10. Ligament graft 10 may be autograft, allograft or artificial graft. The flexible loop is connected to the bone tendon graft 20 and may be attached to the bone block 15 at the time of surgery or prior to the surgery (i.e., may be provided pre-assembled or pre-packaged with the bone tendon graft).

Figure 2:
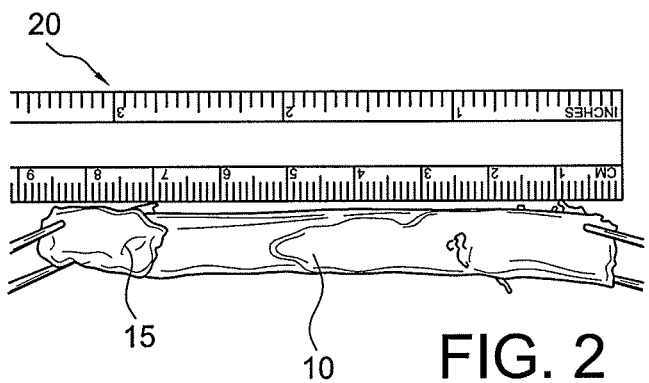

FIGS. 1 and 2 show bone tendon graft 20 before assembling with the suspensory fixation device 50. The ligament portion 10 (the tendinous portion) is about 50 mm long. This length is typically too long to fit into a standard ACL bone tunnel and certainly too long for an all-inside ACL reconstruction.

Figure 3:
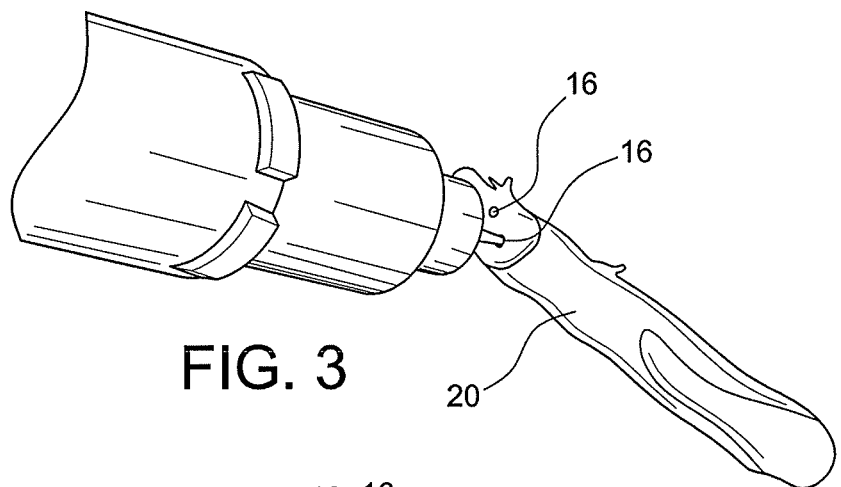
Figure 4:
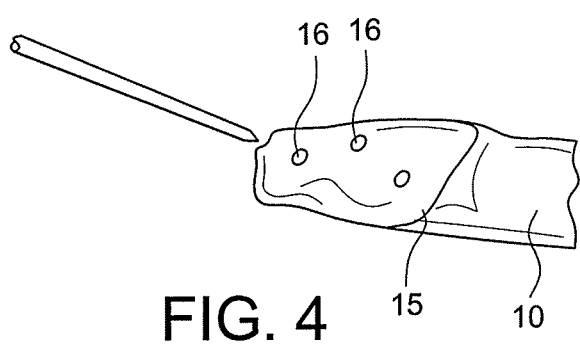

FIGS. 3 and 4 illustrate formation of small drill holes 16 in the bone block 15 of the bone tendon graft 20.

Figure 5:
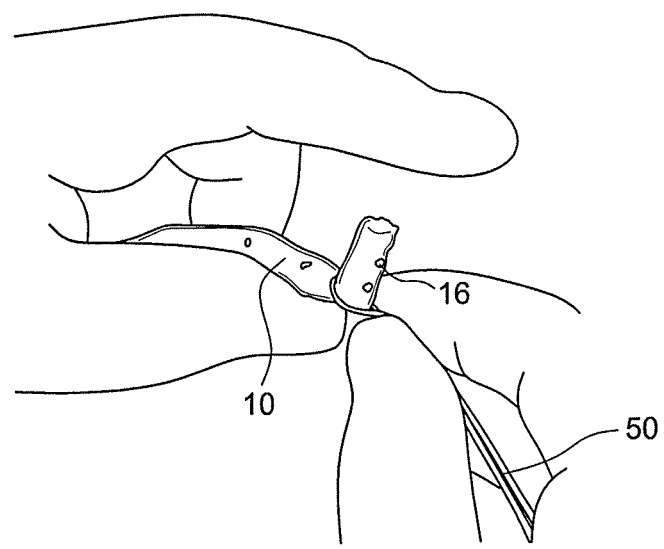
Figure 6:
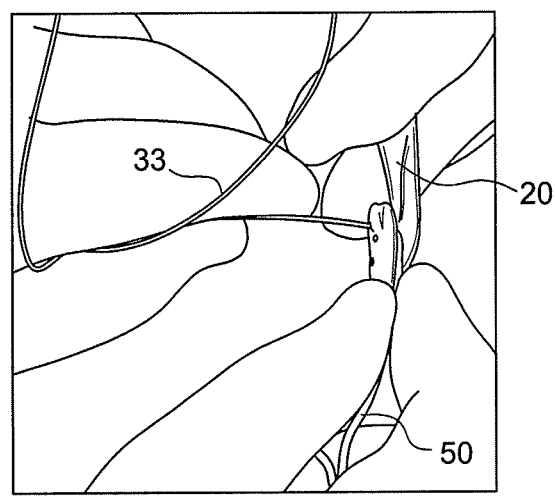
Figure 7:
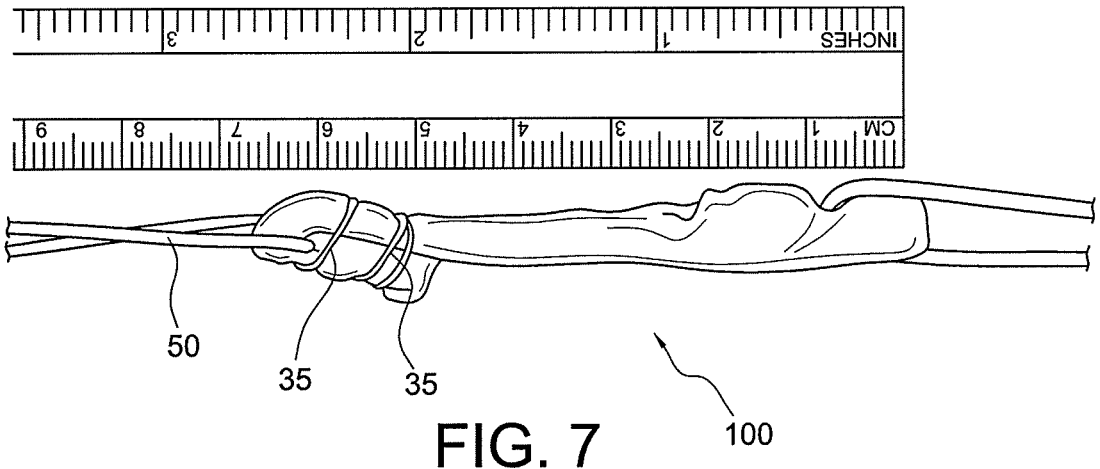

FIGS. 5 and 6 illustrate how the bone block 15 is folded/flipped over fixation device 50, i.e., a suspensory device in an exemplary-only form of an ACL TightRope® 50 (i.e., suspensory fixation device 50 is folded into the crease of the bone tendon graft 20 when the bone block is rotated for about 180 degrees onto the tendon portion). A flexible strand 33, for example, a FiberLoop® suture 33, is then used to suture the bone plug 15 to the tendon 10 by passing the needle through the holes 16 in the bone 15. If using a FiberLoop®, a SpeedWhip™ technique may be used to form a suturing pattern such as pattern 35 of FIG. 7.

Figure 8:
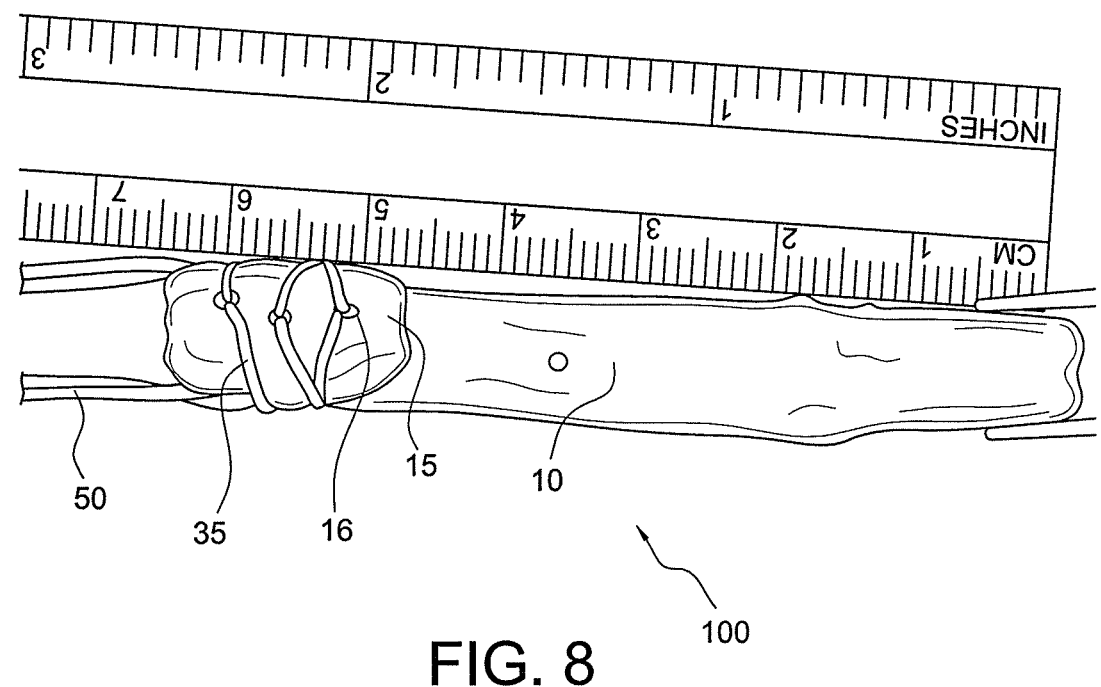
Figure 9:
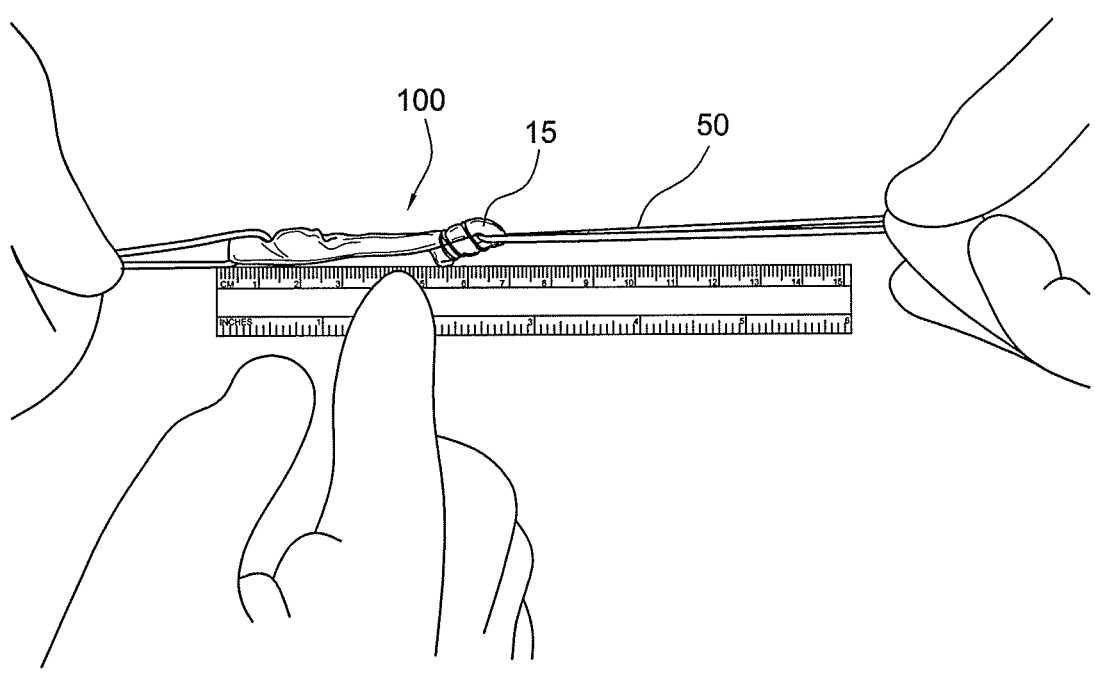

FIGS. 8 and 9 show the overall construct 100 with the tendon 10 shortened significantly and the suspensory fixation device 50 attached. The tendon 10 has a final length L2 which is shorter than the initial length L1 by at least a length 1 of the bone block 15. The FiberLoop® sutures may also be used for fixation if the tails are left intact.

The other end of the bone tendon graft may be attached to similar or different suspensory fixation devices, for example, to knotless suture constructs which include sutures that are spliced—at least in part—in a manner similar to an Arthrex ACL TightRope®, such as disclosed in U.S. Pat. No. 8,439,976, issued May 14, 2013 and U.S. Pat. No. 8,460,379, issued Jun. 11, 2013, the disclosures of which are incorporated in their entireties by reference herein.

If a BTB graft is employed in lieu of the bone tendon graft 20, the technique and steps of the present invention may be applied similarly to both bone blocks, at each end of the BTB construct. Alternatively, one end may undergo the technique of the present invention of flipping the bone block over the suspensory fixation device to shorten the length, while the other end may undergo attachment to a similar or different fixation device by any other known method in the art, including attachment/passing of the fixation device through the bone block (such as BTB TightRope®, for example).

The reconstruction system 100 of the present invention may be provided in a pre-assembled form (pre-packaged) to the surgeon, i.e., with the suspensory fixation device 50 already secured into the crease of the bone tendon graft 20. The reconstruction system 100 may be part of a kit that includes construct 100 with passing sutures attached to the graft.

Suspensory fixation device 50 may include a flexible material which may be a absorbable or nonabsorbable, natural or synthetic, monofilament strand, multifilament strand, a braid or a high strength suture such as FiberWire® suture, sold by Arthrex, Inc. of Naples, Fla., or any combination thereof. The flexible material may be employed with additional fixation devices such as buttons, loops, etc.

Figure 10:
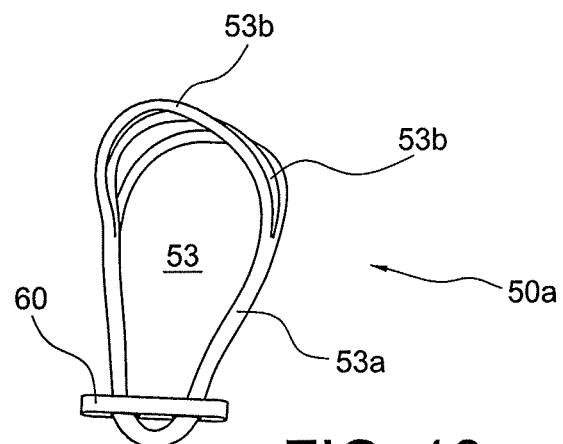
FIGS. 10 and 11 illustrate exemplary suspensory fixation devices for the reconstruction system of FIGS. 1-9.
Figure 11:
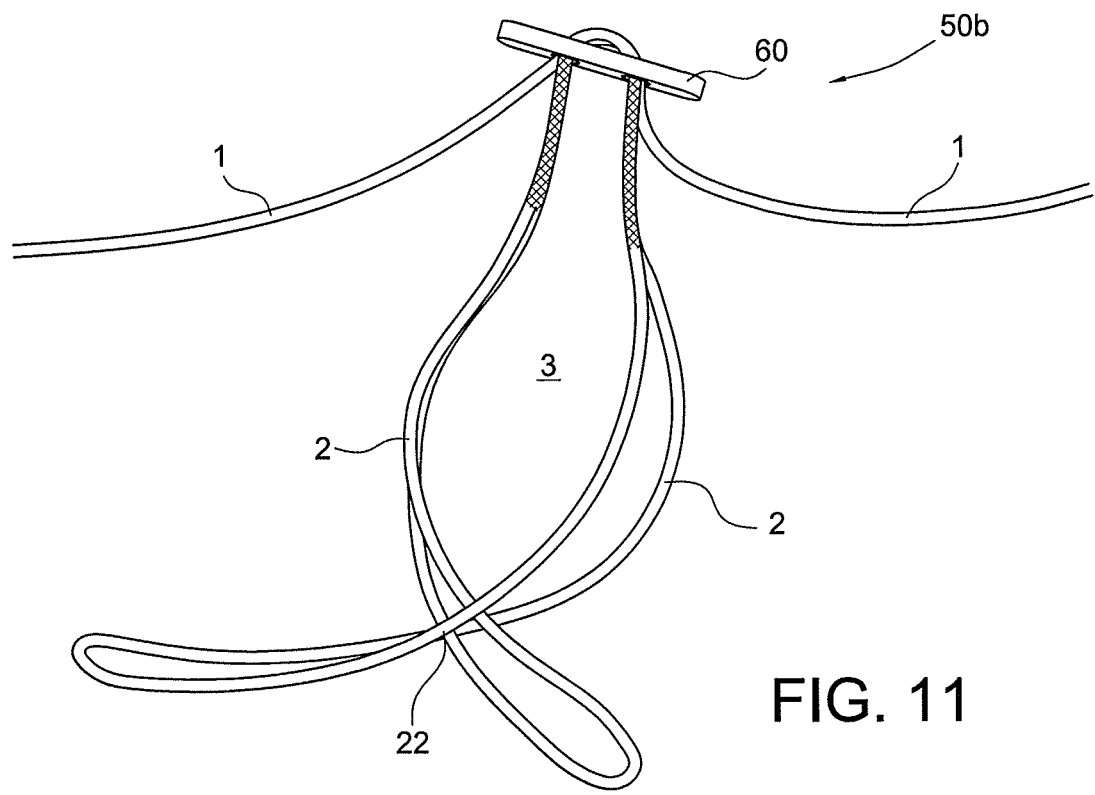

FIGS. 10 and 11 illustrate exemplary suspensory fixation device 50 of the present invention in the form of two exemplary-only tensionable constructs 50a (FIG. 10) and 50b (FIG. 11; ACL TightRope® 50b), which may be each employed for the formation of surgical integrated system 100 of the present invention.

Figure 12:
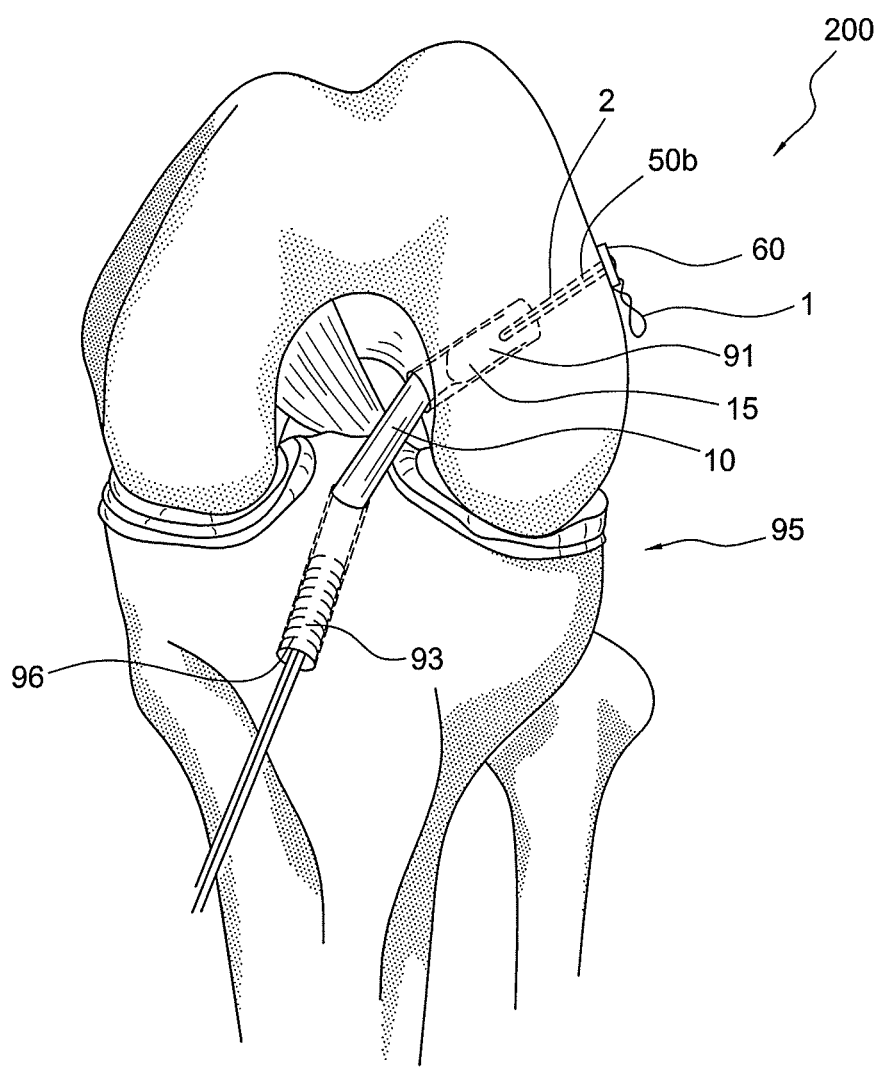
FIG. 12 illustrates the assembly of FIG. 9 provided within femoral and tibial sockets/tunnels according to a method of the present invention.

Tensionable construct 50a is formed of a button 60 with at least two eyelets that allow passage of a continuous loop (preferably a suture loop) that may be a single loop or formed of a plurality of suture strands configured to separate from a single strand to a plurality of strands in a continuous loop. For example, and as shown in FIG. 10, the continuous loop 53 comprises a braided strand 53a of suture (such as FiberWire®, for example) that is configured to trifurcate from one single strand to three strands 53b. In this exemplary "three strand" design, the continuous loop is configured to pass through the button component at the single strand section of the loop, as shown in FIG. 12. In additional embodiments, the continuous loop of the present invention may include suture filaments of various colors.

In the particular exemplary embodiment illustrated in FIG. 11, tensionable construct 50b is a knotless, self-locking, adjustable button/loop construct which consists of button 60 and flexible material 1 with two adjustable eyesplices 2 that are interconnected to form one adjustable loop 3. By pulling on the free braid strands 1, the individual eyesplices 2 constrict and, in turn, reduce the loop length of loop 3. In order for loop 3 to elongate, a force needs to be applied interior to one or both of the eyesplices 2 to elongate the individual loops.

Knotless, self-locking, adjustable button/loop construct 50b comprises two independently-formed and interconnected loops 2, each of the loops 2 having an adjustable length relative to each other. The construct allows adjustment in one direction while preventing or locking the construct from loosening in the opposite direction, due to applied tensile forces. To form knotless suture construct 50b, a flexible strand (braid) 1 is first passed through the button 60 and the strands of the braid are looped around one another. Each end of the braid is spliced through itself, traveling in the direction back towards the original hole passed through in button 60. Each end of the braid is passed through the opposite button hole and down towards interconnected braid loops 2. The final construct 50b with eyesplice interconnection 22 is shown in FIG. 11.

The knotless, self-locking, adjustable button/loop construct is formed of a knotless, closed, adjustable loop 3 that has an adjustable perimeter and length, and is capable of adjusting tension. Details for the formation of adjustable closed loop constructs (similar to the loop 3) are set forth, for example, in U.S. Pat. No. 8,439,976, issued May 14, 2013 and U.S. Pat. No. 8,460,379, issued Jun. 11, 2013, the disclosures of which are incorporated in their entireties by reference herein.

A passing suture (for example, a FiberWire® suture) may be also provided for pulling the button 60 through the bone tunnel or socket (for example, the femoral tunnel). The passing suture (not shown) is removed at the end of the implantation of the final construct.

The pre-assembled construct (tensionable construct 50a, 50b) is then provided to medical personnel in the OR (for example, surgeon) who then completes the final assembly to create the final implantable construct with the graft. The graft may be a BTB graft or any other soft tissue grafts (for example, a bone-tendon graft or a synthetic graft).

The present invention also provides methods of tissue repair/reconstruction by inter alia: (i) providing a surgical reconstruction system comprising a suspensory fixation device including at least one loop; and (ii) securing a bone tendon graft with the reconstruction system and without passing the loop through a bone block of the bone tendon graft.

An exemplary method of tissue repair/reconstruction of the present invention comprises inter alia the steps of: (i) providing a surgical reconstruction system comprising an adjustable, self-locking, knotless loop construct including an adjustable loop formed of two interconnected loops and two splices and, optionally, a button attached to the adjustable loop; and (ii) securing a bone tendon graft with the reconstruction system and without passing the adjustable loop through a bone block of the bone tendon graft.

An exemplary method of ACL reconstruction comprises inter alia the steps of: (i) providing a flexible, adjustable, knotless button/loop construct 50b with a fixation device (button) 60 attached to the button/loop construct that is capable of adjusting tension, the button/loop construct 50b including an adjustable loop and two corresponding eyesplices; (ii) folding a bone block 15 of a bone tendon graft 20 over the button/loop construct 50b; (iii) using a flexible strand 33 to secure the bone block 15 to the button/loop construct 50b and form surgical integrated system 100; and (iv) securing the surgical integrated system 100 within a femoral tunnel/socket by pulling on button 60. The construct is adjustable in length and allows the surgeon the ability to customize the device to each patient and seat the bone block fully against the back wall of the femoral socket. The adjustments are self-locking and the fixation device (implant) minimizes the compressive forces on the bone block.

FIG. 12 illustrates surgical construct 100 of the present invention (a bone tendon graft 20 attached to a suspensory device 50b) being introduced and secured into both a femoral tunnel/socket 91 and a tibial tunnel/socket 93 of knee 95 (typically through an arthroscopic portal). The button 60 is pulled out of the bone cortex with the passing sutures (which are later discarded) and self-flips onto the femoral cortex immediately upon exiting. The length of the flexible material 1 is adjusted by being shortened by applying tension to the strands. The distal strands of the flexible material 1 may be further tensioned utilizing an instrument such as a suture tensioner. The bone block 15 occludes the socket/tunnel 91 to prevent fluid extravasation. If a BTB construct is employed, two bone blocks 15 would occlude the femoral and tibial tunnel/socket 91, 93. On the tibial side, the surgical integrated construct 100 may be secured to the tibial tunnel/socket 93 with additional fixation device such as interference screw 96, for example.

Button 60 of the reconstruction integrated assembly 100 may be formed, for example, of metal, PEEK or PLLA. As detailed above, the button is provided with openings that allow the passage of the flexible materials to pass thereto. The flexible materials may be a high strength braid construct such as an ultrahigh molecular weight (UHMWPE) braid. The flexible materials may be provided with optional colored strands (for example, white and blue) to assist surgeons in distinguishing between suture lengths with the trace and suture lengths without the trace.

The flexible strands employed for the constructs of the present invention may be formed of a high-strength suture, such as an ultrahigh molecular weight polyethylene (UHMWPE) suture which is the preferred material as this material allows easy splicing. Alternatively, the high strength suture may be a FiberWire® suture, which is disclosed and claimed in U.S. Pat. No. 6,716,234, the entire disclosure of which is incorporated herein by reference. FiberWire® suture is formed of an advanced, high-strength fiber material, namely ultrahigh molecular weight polyethylene (UHMWPE), sold under the tradenames Spectra (Honeywell) and Dyneema (DSM), braided with at least one other fiber, natural or synthetic, to form lengths of suture material. The preferred FiberWire® suture includes a core within a hollow braided construct, the core being a twisted yarn of UHMWPE.

The strands may also be formed of a stiff material, or combination of stiff and flexible materials, depending on the intended application. The strands may be also coated and/or provided in different colors. The knotless constructs of the present invention can be used with any type of flexible material or suture that forms a splice and a loop.

The knotless suture constructs also include sutures that are spliced—at least in part—in a manner similar to an Arthrex ACL TightRope®, such as disclosed in U.S. Pat. No. 8,439,976, issued May 14, 2013 and U.S. Pat. No. 8,460,379, issued Jun. 11, 2013, the disclosures of which are incorporated in their entireties by reference herein.

The reconstruction system 100 may be employed on site for ACL reconstructions, for example, which otherwise would not be possible because of the length of the tendon. In an exemplary ACL repair, the reconstruction system 100, of the present invention may be introduced into a socket/tunnel in the femur of the knee (usually through an arthroscopic portal). The button attached to the ACL TightRope® 50b, together with the portion of the closed loop connected to the button, are pulled out of the bone cortex with the passing sutures (later discarded). Upon exiting the hole in the bone cortex, the button, closed loop and passing sutures decompress, securing the button against the surface of the bone and fixing the construct in place. The graft 10 attached to bone block 15 is advanced further into the femoral and tibial sockets/tunnels and secured with additional fixation devices (such as interference screws, for example) to the walls of the sockets/tunnels, as is known in the art. On the tibial side, another button/loop fixation may be conducted to attach the other end of the construct 100. If desired, a regular BTB TightRope® construct may be employed on the other end of the construct 100, i.e., with the loop going through the bone block and not provided into the crease of the bone tendon graft.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting.

What is claimed is:

1. A pre-assembled tensionable construct comprising:
   a button,
   a suture construct with a knotless, adjustable closed suture loop connected to the button, and
   a bone tendon construct attached to the suture loop without passage of the suture loop through any portion of the bone tendon construct,
   wherein the bone tendon construct includes
      a bone block integral with a tendon, wherein the bone block is rotated over a portion of the suture loop and onto the tendon to establish a crease within a folded portion of the bone tendon construct, the folded portion of the bone tendon construct is located at an interface between the bone block and the tendon, and the portion of the suture loop is positioned within the crease within the folded portion of the bone tendon construct; and
      a plurality of sutures through the bone block and through the tendon to secure the bone block to the tendon.

2. The pre-assembled tensionable construct as recited in claim 1, wherein the bone tendon construct includes an initial length before rotating the bone block and a final length after rotating the bone block, wherein the final length is shorter than the initial length by at least a length of the bone block.

3. The pre-assembled tensionable construct as recited in claim 2, wherein the bone block is rotated about 180 degrees onto the tendon.

4. A method of tissue repair, comprising the steps of:
   providing the pre-assembled tensionable construct of claim 1,
   inserting the pre-assembled construct within a first bone tunnel and a second bone tunnel; and
   adjusting a length of the suture loop to secure the pre-assembled construct within the first and second bone tunnels.

5. The method of claim 4, wherein the step of securing the bone block to the tendon further comprises the steps of providing at least one through hole through the bone block; and passing at least one flexible strand through the at least one through hole and through the tendon, to form a stitching pattern connecting the bone block to the tendon.

6. The method of claim 4, wherein the knotless, adjustable loop has an adjustable perimeter.

7. The method of claim 4, wherein the knotless, adjustable loop is formed by the steps of:
   providing the suture loop having two ends;
   attaching one end to a suture passing device;
   passing the suture passing device through the center of the suture loop to form a first eyesplice with one of the two ends;
   sliding the button over a non-spliced strand so that the button rests over the spliced strand; and
   passing the suture passing device through the center of the first eyesplice to form a second eyesplice with the other of the two ends, wherein the first eyesplice is interconnected to the second eyesplice.

8. The method of claim 4, wherein the bone tendon construct is a BTB graft.

9. The method of claim 4, wherein the bone construct includes soft tissue, graft, tendon, ligament, synthetic material, biological material, bone, or a combination of such materials.

10. A reconstruction system for tissue repairs, comprising:
    a button;
    a loop connected to the button;
    a bone tendon graft including a bone block integral with a tendinous portion, the bone tendon graft attached to the loop without passing the loop through either of the bone block or the tendinous portion, the bone block rotated over a portion of the loop onto the tendinous portion to establish a crease within a folded portion of the bone tendon graft, the folded portion located at an interface between the bone block and the tendinous portion,
    and wherein the portion of the loop is positioned within the crease; and
    a flexible strand separate from the loop and extending through the bone block and the tendinous portion to secure the bone block to the tendinous portion.

11. The reconstruction system as recited in claim 10, wherein the loop is a fixed loop.

12. The reconstruction system as recited in claim 10, wherein the loop is an adjustable loop.

13. The reconstruction system as recited in claim 10, wherein the flexible strand passes through drill holes in the bone block.

14. The reconstruction system as recited in claim 10, wherein, once rotated, the bone block extends from the folded portion proximally along a surface of the tendinous portion toward an end of the tendinous portion that is opposite from the folded portion.

15. The reconstruction system as recited in claim 10, wherein a first end of the bone tendon graft is attached to the loop, and a second end of the bone tendon graft is attached to a second loop.

16. The reconstruction system as recited in claim 15, wherein the second loop is connected to a second button.

17. The reconstruction system as recited in claim 10, wherein the loop is a flexible loop having at least one splice with an adjustable length.

18. The reconstruction system as recited in claim 10, wherein the flexible strand forms a suturing pattern around the bone block and the tendinous portion.

19. The reconstruction system as recited in claim 10, wherein the bone tendon graft includes an initial length prior to rotating the bone block and a final length after rotating the bone block, wherein the final length is shorter than the initial length by at least a length of the bone block.

20. The reconstruction system as recited in claim 10, wherein the bone block includes an outer face that faces in a direction away from the tendinous portion before rotating the bone block, and the outer face is contiguous with the tendinous portion after rotating the bone block.

21. The reconstruction system as recited in claim 10, wherein the flexible strand is part of a continuous suture loop.

22. The reconstruction system as recited in claim 21, wherein the continuous suture loop establishes a whip-stitched suture pattern in the bone tendon graft.

23. A reconstruction system for tissue repairs, comprising:
a button;
a loop connected to the button;
a bone tendon graft attached to the loop and including a bone block integral with a tendinous portion attached to the bone block,
wherein the bone tendon graft is attached to the loop without passing the loop through either of the bone block or the tendinous portion of the bone tendon graft,
wherein the bone tendon graft includes a folded portion located at an apex of the bone tendon graft,
wherein a portion of the loop is positioned within a crease located immediately inward from the apex and at an interface between the bone block and the tendinous portion; and
a suture pattern extending through both the bone block and the tendinous portion for securing the bone block to the tendinous portion,
wherein the suture pattern is separate from any portion of the loop,
wherein each stitch of the suture pattern is located further from the apex than the portion of the loop that is positioned within the crease.

* * * * *